(12) United States Patent
Bogardus et al.

(10) Patent No.: US 6,207,650 B1
(45) Date of Patent: Mar. 27, 2001

(54) ANTIVIRAL, HIGHLY WATER SOLUBLE, STABLE, CRYSTALLINE SALTS OF 2', 3'-DIDEOXYINOSINE, 2', 3'-DIDEOXY-2', 3'-DIDEHYDROTHYMIDINE AND 2', 3'-DIDEOXY-2'-FLUOROINOSINE

(75) Inventors: Joseph B. Bogardus, Manlius; Murray A. Kaplan, Syracuse; Robert K. Perrone, Liverpool, all of NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 07/805,729

(22) Filed: Dec. 6, 1991

Related U.S. Application Data

(63) Continuation-in-part of application No. 07/772,641, filed on Oct. 8, 1991, now abandoned, which is a continuation of application No. 07/652,454, filed on Feb. 7, 1991, now abandoned, which is a continuation of application No. 07/514,261, filed on May 1, 1990, now abandoned, which is a continuation-in-part of application No. 07/352,065, filed on May 15, 1989, now abandoned.

(51) Int. Cl.[7] .................. A61K 31/70; C07H 19/073; C07H 19/173; C07H 19/20
(52) U.S. Cl. .................. 514/45; 514/50; 536/27.14; 536/27.8; 536/28.2; 536/28.54
(58) Field of Search .................. 536/23, 24, 27.14, 536/27.8, 28.2, 28.54; 514/45, 50

(56) References Cited

U.S. PATENT DOCUMENTS

| | | | |
|---|---|---|---|
| 3,817,982 | * 6/1974 | Verheyden et al. | 536/23 |
| 4,861,759 | 8/1989 | Mitsuya et al. | 514/46 |
| 4,978,655 | 12/1990 | Lin et al. | 514/50 |

FOREIGN PATENT DOCUMENTS

| | | | |
|---|---|---|---|
| 31973/84 | * 8/1984 | (AU) | . |
| 1262132 | * 10/1989 | (CA) | . |
| 0273277 | * 7/1988 | (EP) | . |
| 0287313 | 10/1988 | (EP) | . |
| 2109369 | * 6/1983 | (GB) | . |
| 87/01284 | * 3/1987 | (WO) | . |

OTHER PUBLICATIONS

Suzuki et al., *Bull. Chem. Soc. Japan*, 47,(10), 2556–2558 (1974).*
Waqar et al., *J. Cellular Physiology*, 121, 402–408 (1984).*
Hamamoto et al., *Antimicrobial Agents and Chemotherapy*, 31(6), 907–910 (1987).*
Baba et al.(I), *Antimicrobial Agents and Chemotherapy*, 31(10), 1613–1617 (1987).*
Lin et al., *Biochemical Pharmacology*, 36(17), 2713–2718 (1987).*
Baba et al.(II), *Biochemical Biophysical Res. Comm.*, 142(1), 128–134 (1987).*
Balzarini et al., *Biochemical and Biophysical Res. Comm.*, 158(2), 413–422 (Jan. 1989).*
March, *Advanced Organic Chemistry*, McGraw–Hill Book Co., New York, New York, 1968, see chapter 8.*
DeClercq, J., *Antimicrobial Chemotherapy*, Suppl. A, 23, 35–46 (1989).*

* cited by examiner

*Primary Examiner*—Gary Geist
*Assistant Examiner*—L. Eric Crane
(74) *Attorney, Agent, or Firm*—David M. Morse; Sandra M. Nolan

(57) ABSTRACT

Provided are very highly water soluble, stable, crystalline salts of 2',3'-dideoxy-2',3'-didehydrothymidine ("d4T"), 2',3'-dideoxyinosine ("ddI"), and 2',3'-dideoxy-2'-fluoroinosine ("F-ddI"). Such salts are useful as intermediates or as antiviral agents.

24 Claims, 13 Drawing Sheets

ANTIVIRAL, HIGHLY WATER SOLUBLE, STABLE, CRYSTALLINE SALTS OF 2', 3'-DIDEOXYINOSINE, 2', 3'-DIDEOXY-2', 3'-DIDEHYDROTHYMIDINE AND 2', 3'-DIDEOXY-2'-FLUOROINOSINE

CROSS-REFERENCE TO RELATED APPLICATIONS

This application is a continuation-in-part application of application, U.S. Ser. No. 07/772,641, filed Oct. 8, 199, abandoned, which is a continuation application of U.S. Ser. No. 07/652,454, filed Feb. 7, 1991, now abandoned, which is a continuation of U.S. Ser. No. 07/514,261, file May 1, 1990, now abandoned, which is a continuation-in-part application of U.S. Ser. No. 07/352,065, filed May 15, 1989, now abandoned.

BACKGROUND OF THE INVENTION

The present invention concerns highly water soluble, stable, crystalline antiviral (including antiretroviral) salts of 2',3'-dideoxyinosine, 2',3'-dideoxy-2',3'-didehydrothymidine and 2',3'-dideoxy-2'-fluoroinosine, particularly sodium or potassium salts thereof.

Infectious viral diseases are recognized as an important medical problem. Progress against infectious viral disease requires the development of drugs with selective antiviral activity, while remaining benign to normal cell lines. A number of antiviral agents currently under study which seem to possess some selectivity are nucleoside analogs. In general, these compounds are structural analogs of the naturally occurring nucleosides. Structural modification in either the purine or pyrimidine base nucleus and/or the saccharide component results in a synthetically modified nucleoside derivative which, when incorporated into a viral nucleic acid forming process, acts to disrupt further synthesis of viral nucleic acid.

Effectiveness of these antiviral agents depends on selective conversion by viral enzymes, but not by host enzymes, to the corresponding nucleotide analog which is then converted to the triphosphate followed by incorporation into viral nucleic acid. A problem with this antiviral strategy has been the emergence of certain viral strains whose enzymes poorly promote phosphorylation of the nucleoside analogs. To circumvent this problem, intact nucleotide analogs appear to be potentially quite useful as antivirals for incorporation into viral nucleic acid.

PCT application WO 87/01284 to Mitsuya and Broder describes the use of 2',3'-dideoxyinosine ("ddI") for use against AIDS.

EP 0 273 277 to Lin and Prusoff discloses the use of 2',3'-dideoxy-2',3'-didehydrothymidine ("d4T") in treating patients infected with a retrovirus.

Erik De Clercq, "Potential Drugs for the Treatment of AIDS", *Journal of Antimicrobial Chemotherapy*, 23, Suppl. A, 35–46, (1989), describes the use of dideoxynucleoside analogues to inhibit the infectivity and cytopathic effect of human immunodeficiency virus ("HIV")

EP 0 287 313 discloses 2',3'-dideoxy-2'-fluoroinosine ("F-ddI") and its activity against HIV.

SUMMARY OF THE INVENTION

The present invention concerns very highly water soluble, stable, crystalline salts of 2',3'-dideoxy-2',3'-didehydrothymidine ("d4T") of Formula (I):

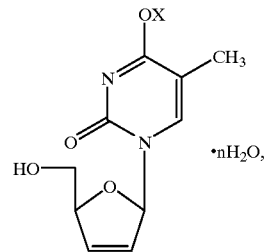

2',3'-dideoxyinosine ("DDI") of Formula (II):

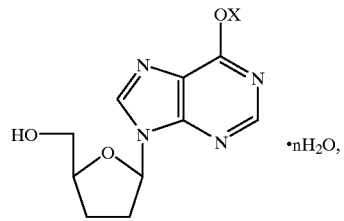

and 2',3'-dideoxy-2'-fluoroinosine ("F-ddI") of Formula (III):

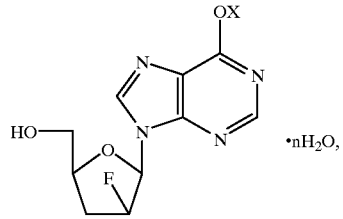

wherein X is a cation, e.g., $Na^+$, $K^+$, $Mg^{++}$, $Ca^{++}$ or amine, and n is 0.5 to 2.0.

The present invention also concerns pharmaceutical compositions comprising an antiviral effective amount of such salts and a solid, liquid or gaseous physiologically acceptable diluent.

Still further, the present invention relates to a method of treating a warm blooded animal, for example, a human, comprising administering to such warm blooded animal an antiviral effective amount of one of the aforesaid salts.

DETAILED DESCRIPTION OF THE INVENTION

Figure 1:
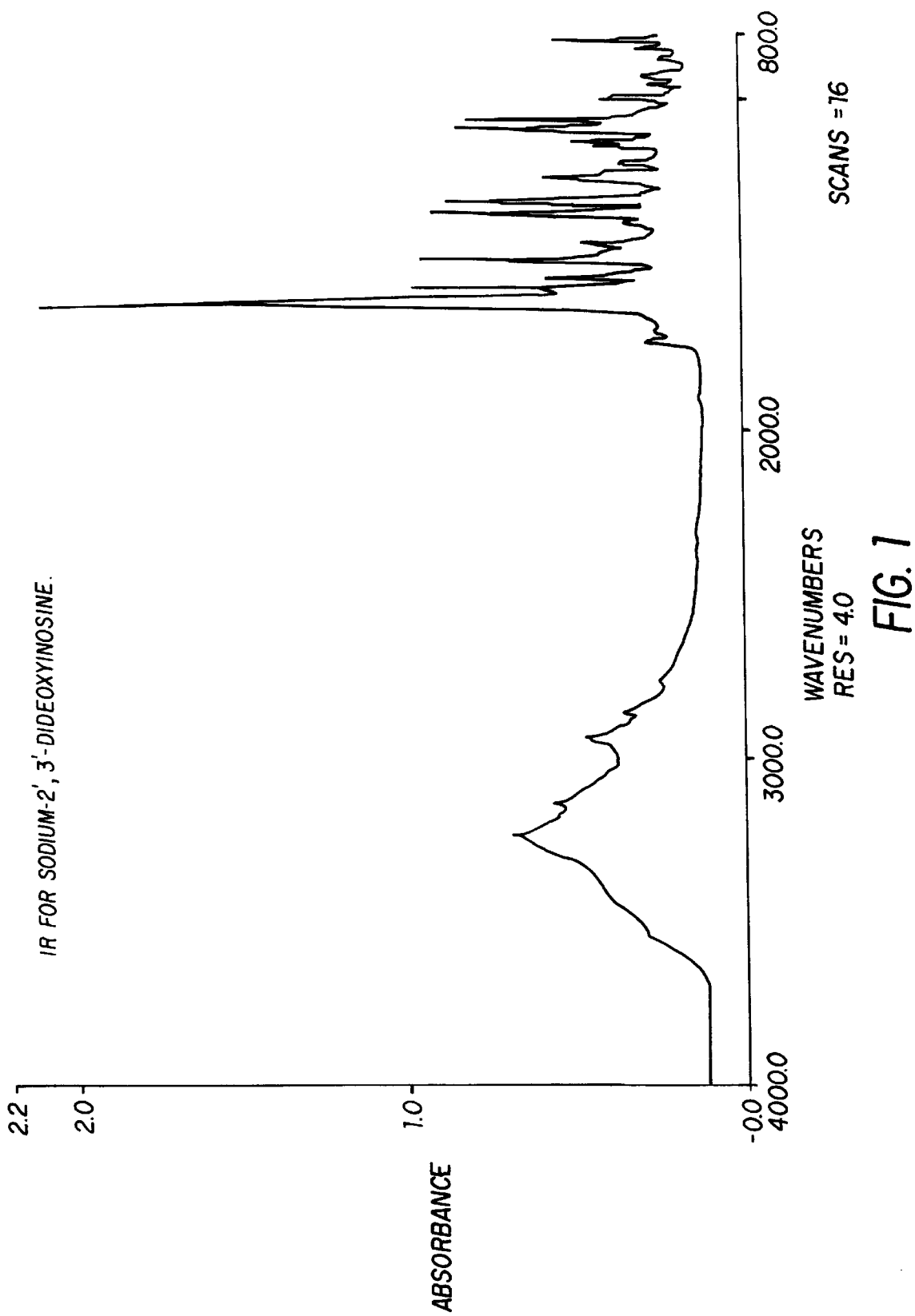
FIG. 1 depicts an IR for sodium 2',3'-dideoxyinosine.

As indicated above, the present invention pertains to pharmaceutically acceptable non-toxic salts of 2',3'-dideoxyinosine, 2',3'-dideoxy-2',3'-didehydrothymidine and 2',3'-dideoxy-2'-fluoroinosine containing, for example, $Na^+$, $Li^+$, $K^+$, $Ca^{++}$ and $Mg^{++}$. Such salts may include organic cations and also those containing an appropriate cation such as an alkali or alkaline earth metal ion or an ammonium or a quaternary amino ion. The preferred salt is the sodium salt. Metal salts can be prepared by reacting the metal hydroxide with 2',3'-dideoxyinosine, 2',3'-dideoxy-2',3'-didehydrothymidine or 2',3'-dideoxy-2'-fluoroinosine. A less soluble metal salt can be precipitated from the solution of a more soluble salt by addition of the suitable metal ion.

The compounds of this invention have desirable antiviral activity. They exhibit activity against viruses, for example, Herpes Simplex virus I, Herpes Simplex virus II, cytomegalovirus, Varicella Zoster virus, influenza virus, vaccinia, polio, rubella, smallpox, cowpox, Epstein-Barr virus, measles virus, human respiratory virus, papillomavirus and Sinbis virus, just to mention a few and also against retroviruses, for example, human immunodeficiency virus (HIV).

As mentioned above, the compounds of the present invention are useful active ingredients in human and veterinary medicine for the treatment and prophylaxis of diseases caused by retroviruses. Examples of fields of indication in human medicine regarding retroviruses are as follows:

(1) the treatment or prophylaxis of human retrovirus infections;

(2) the treatment or prophylaxis of diseases caused by HIV (previously called HTLV-III/LAV or AIDS) and the stages associated therewith such as ARC (AIDS related complex) and LAS (lymphadenopathy syndrome) and the immune weakness and encephalopathy caused by this retrovirus;

(3) the treatment or prophylaxis of HTLV-I infection or HTLV-II infection;

(4) the treatment or prophylaxis of the AIDS carrier state (AIDS transmitter state); and (5) the treatment or prophylaxis of diseases caused by hepatitis B virus.

Examples of indications in veterinary medicine are as follows:

(1) Maedivisna (in sheep and goats), (2) progressive pneumonia virus (PPV) (in sheep and goats), (3) caprine arthritis encephalitis virus (in sheep and goats), (4) Zwoegerziekte virus (in sheep), (5) infectious virus of anemia (of the horse), and (6) infections caused by cat leukemia virus.

For use against viral infections the compounds of 30 this invention can be formulated into pharmaceutical preparations. Such preparations are composed of one or more of the inventive compounds in association with pharmaceutically acceptable carriers. The reference *Remington's Pharmaceutical Sciences,* 17th Edition, A. R. Gennaro, editor (Mack Publishing Company, 1985) discloses typical carriers and methods of preparation.

The compounds of the invention are administered systemically to warm blooded animals, e.g., humans. By systemic administration is intended oral, rectal, and parenteral (i.e., intramuscular, intravenous, subcutaneous and nasal) routes. Generally, it will be found that when a compound of the present invention is administered orally, a larger quantity of the reactive agent may be required to produce the same effect as the smaller quantity given parenterally. In accordance with good clinical practice, it is preferred to administer the instant compounds at a concentration level that will produce an effective antiviral effect without causing any harmful or untoward side effects.

Therapeutically and prophylactically the instant compounds are usually given as pharmaceutical compositions comprised of an effective antiviral amount of a compound according to the invention and one or more pharmaceutically acceptable carriers, as stated hereinabove. Pharmaceutical compositions for effecting such treatment will contain a major or minor amount, e.g., from 100 to 0.5% of at least one compound of the present invention in combination with a pharmaceutical carrier, the carrier comprising one or more solid, semi-solid, or liquid diluents, fillers and formulation adjuvants which are non-toxic, inert and pharmaceutically acceptable.

Such pharmaceutical compositions are preferably in dosage unit form, i.e., physically discrete units containing a predetermined amount of the drug corresponding to a fraction or multiple of the dose which is calculated to produce the desired therapeutic response. Other therapeutic agents can also be present.

Pharmaceutical compositions providing from about 10 mg to 2 grams of the active ingredient per unit dose are preferred and are conventionally prepared as tablets, lozenges, capsules, powders, granules, aqueous or oily suspensions, syrups, elixirs, and aqueous or non-aqueous solutions. Preferred oral compositions are in the form of tablets or capsules and may contain conventional excipients such as binding agents (e.g., syrup, acacia, gelatin, sorbitol, tragacanth or polyvinylpyrrolidone), fillers (e.g., lactose, sugar, corn starch, calcium phosphate, sorbitol, or glycine), lubricants (e.g., magnesium stearate, talc, polyethylene glycol or silica), disintegrants (e.g., starch), buffering agents (inorganic or organic) and wetting agents (e.g., sodium lauryl sulfate). Solutions or suspensions of an inventive compound with conventional pharmaceutical vehicles are employed for parenteral compositions, such as an aqueous solution for intravenous injection or an oily suspension or solution for intramuscular injection. Such compositions having the desired clarity, stability and adaptability for parenteral use are obtained by dissolving from 0.1% to 35% by weight of an active inventive compound in water or a vehicle comprising a polyhydric aliphatic alcohol such as glycerine, propylene glycol, and polyethylene glycol or mixtures thereof. The polyethylene glycols comprise a mixture of non-volatile, usually liquid, polyethylene glycols which are soluble in both water and organic liquids and have molecular weights from about 200 to 1500.

Some of the inventive compounds are prone to acid hydrolysis. For optimum bioavailability, tablets, capsules and granules required for oral dosage should be enteric coated, strongly buffered against gastric acid, or both.

The salts of this patent application are stable, crystalline and of very high water solubility (>200 mg/ml), ideally suited for high concentration, low volume IV-IM injectables. Most importantly, the high alkalinity (pH 9.5–11) of these new and novel salts allow for self-buffering against gastric acid. Thus, less buffer could be required in oral dosage forms.

The salts of the invention are reversibly "immobilized" in the enolic form, and thus, can be considered as intermediates for synthesis of varied potentially bio-active derivatives as enol esters (prodrugs) and enol ethers. The esters and ethers could also function as protecting (blocking) groups, allowing for synthetic work on other functionalities or moieties of the molecule.

Considering the biological activities possessed by the compounds of the instant invention, it can be seen that these compounds have antiviral properties, particularly suited to their use in combating viral infections. Thus, another aspect of the instant invention concerns a process for treating viral (including retroviral) infections in a mammal in need of such treatment which comprises systemic administration to such mammal of an effective dose of an inventive compound.

On the basis of testing, an effective dose could be expected to be from about 0.1 to about 5 mg/kg body weight with about 1 to about 4 mg/kg body weight a preferred dosage range. It is envisioned that for clinical antiviral application, compounds of the instant invention will be administered in the same manner as for the reference drug zidovudine (AZT). For clinical applications, however, the dosage and dosage regimen must in each case be carefully adjusted, utilizing sound professional judgement and consideration of the age, weight and condition of the recipient, the route of administration and the nature and gravity of the illness. Generally a daily oral dose will comprise from about 150 mg to about 5 grams, preferably 10–1500 mg of an inventive compound administered from one to three times a day. In some instances, a sufficient therapeutic effect can be obtained at lower doses, while in others, larger doses will be required.

The compounds which constitute this invention and their methods of preparation will appear more fully from a consideration of the following examples which are given for the purpose of illustration only and are not to be construed as limiting the invention in sphere or scope. All temperatures are understood to be in ° C. when not specified. All compounds gave satisfactory elemental analyses.

EXAMPLE 1

Preparation of Sodium ddI Monohydrate

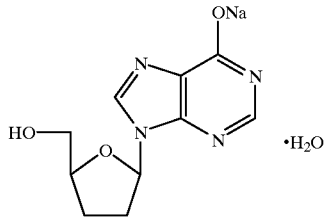

MW: ddI=236.14
MW: NaOH=40

$$\frac{1 \text{ g ddI}}{236.14} = \frac{X}{40} = \frac{169 \text{ mg NaOH}}{40} = \begin{array}{l}\text{4.3 ml of 1 N NaOH is}\\ \text{equivalent to 1 g of}\\ \text{ddI for a 1:1 molar}\\ \text{ratio.}\end{array}$$

1. Add 1 g of ddI to 4.51 ml of aqueous 1 N NaOH (1.05 molar equivalents with moderate stirring at 10–25° C. over a 5 minute interval. A solution (pH 9.5–11), or near solution is obtained.
2. If required, pass the solution through the equivalent of a 0.2–0.45 micron Gelman HT-Tuffryn filter to clarify.

Steps 1 and 2 should be completed within 1.5 hours.

3. Add the Na-ddI solution, over a 10–15 minute interval to 50–75 ml of very vigorously stirred isopropanol (alternatively, acetone could be used). Crystals form. Continue vigorous stirring (closed system) for 2 hours.
4. Collect the crystals via a suitable vacuum filtration procedure. Do not draw excess air through the filter-cake. Tamp the crystalline filter-cake (under vacuum) to remove any cracks or fissures which may form. Do not draw excess air through the cake.
5. Wash the filter-cake with three separate 15 ml portions of isopropanol and then with three separate 20 ml portions of acetone. Do not draw excess air through the filter-cake between washings. Remove by tamping any cracks or fissures which may form between washings.
6. High vacuum dry the crystals at 24–35° C. for 24 hours. Expected yield: 1–1.1 g.
7. If desired, acetone can be totally substituted for the preferred isopropanol and the modes of addition reversed, viz, the solvents added to the stirring aqueous DDI solution over a half-hour interval.

As described above and in specific detail below, KOH and/or other strong organic and inorganic bases can be substituted for NaOH to form the corresponding salts.

Chemical and Physical Properties Obtained for Sodium ddI.$H_2O$

1. Water Solubility: >300 mg/ml (pH 9.5–11)
2. Aqueous Solution Stability:
   5% loss for 1 week at 50° C.;
   10% loss for 1 week at 70° C.
3. Solid State Stability: No loss for 5 weeks at 70° C.
4. Elemental Analysis: $C_{10}H_{11}N_4O_3Na.H_2O$ ($C_{10}H_{13}N_4O_4Na$) MW –276.26

|  | Theory | Found |
|---|---|---|
| % C | 43.5 | 43.18 |
| % H | 4.7 | 4.6 |
| % N | 20.3 | 20.16 |
| % Na (Ash) | 8.3 | 8.26 |
| % $H_2O$ KF | 6.5 (for monohydrate) | 6.57 |

Figure 2:
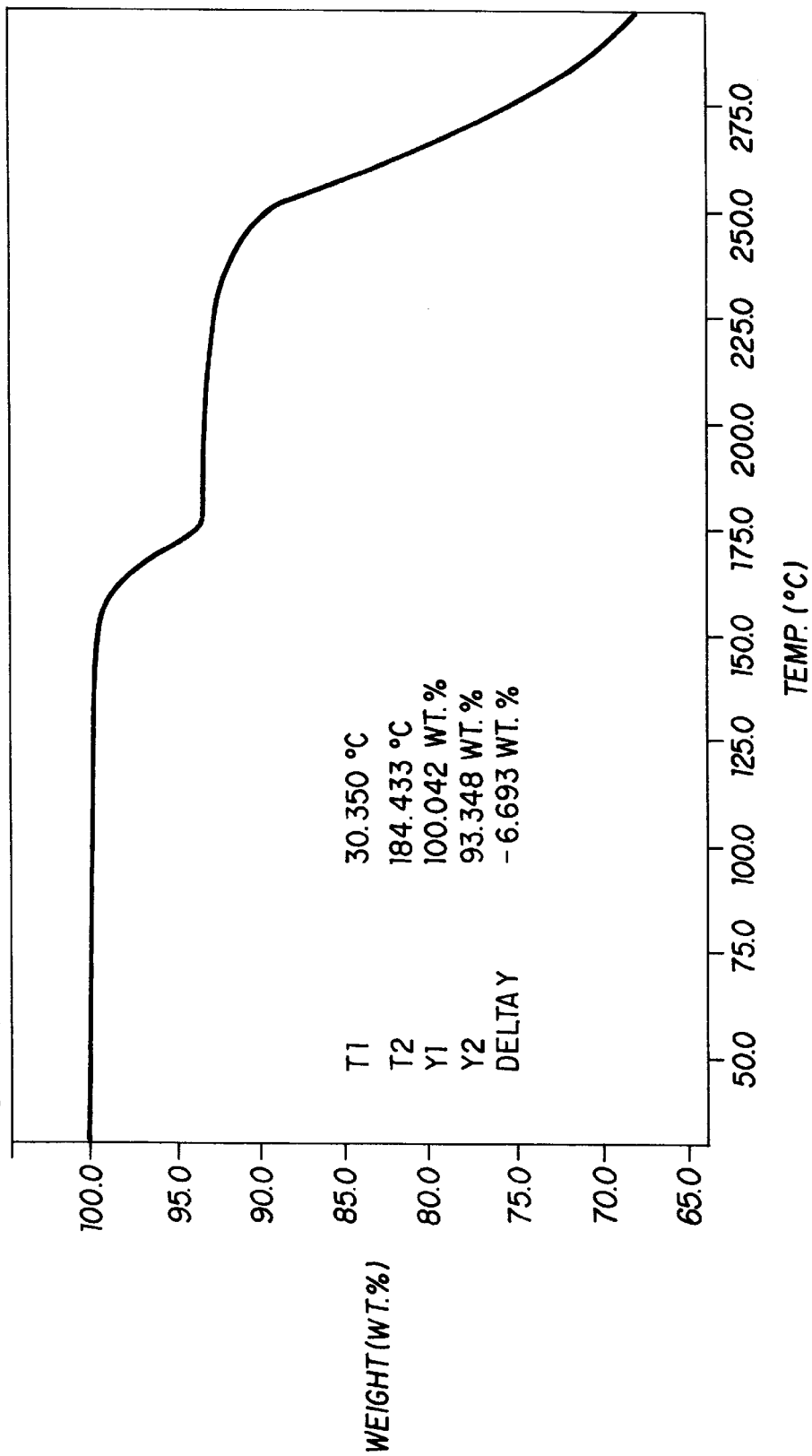
FIG. 2 depicts a TGA for sodium 2',3'-dideoxyinosine.
Figure 3:
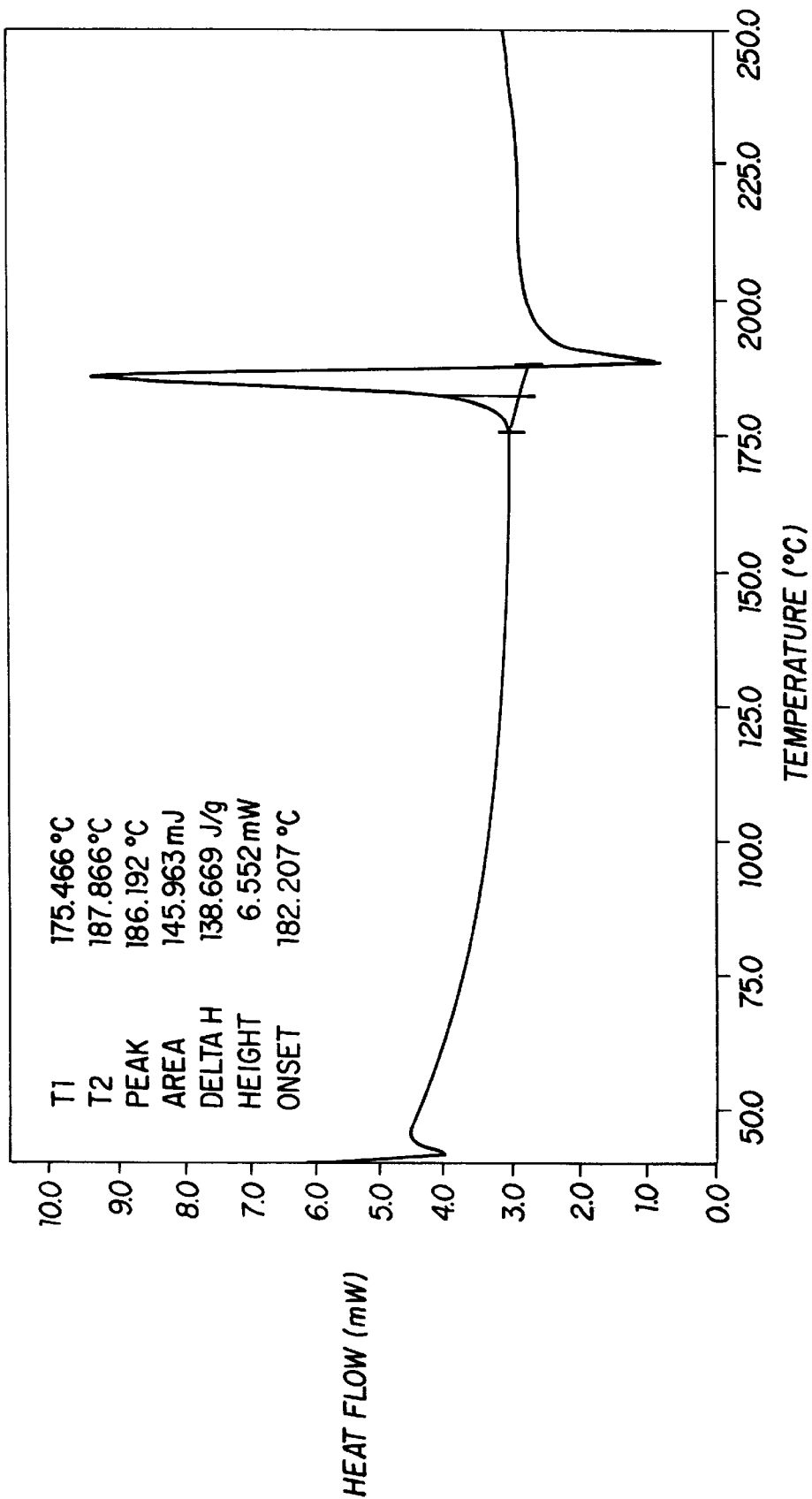
FIG. 3 depicts a DSC for sodium 2',3'-dideoxyinosine.
Figure 6:
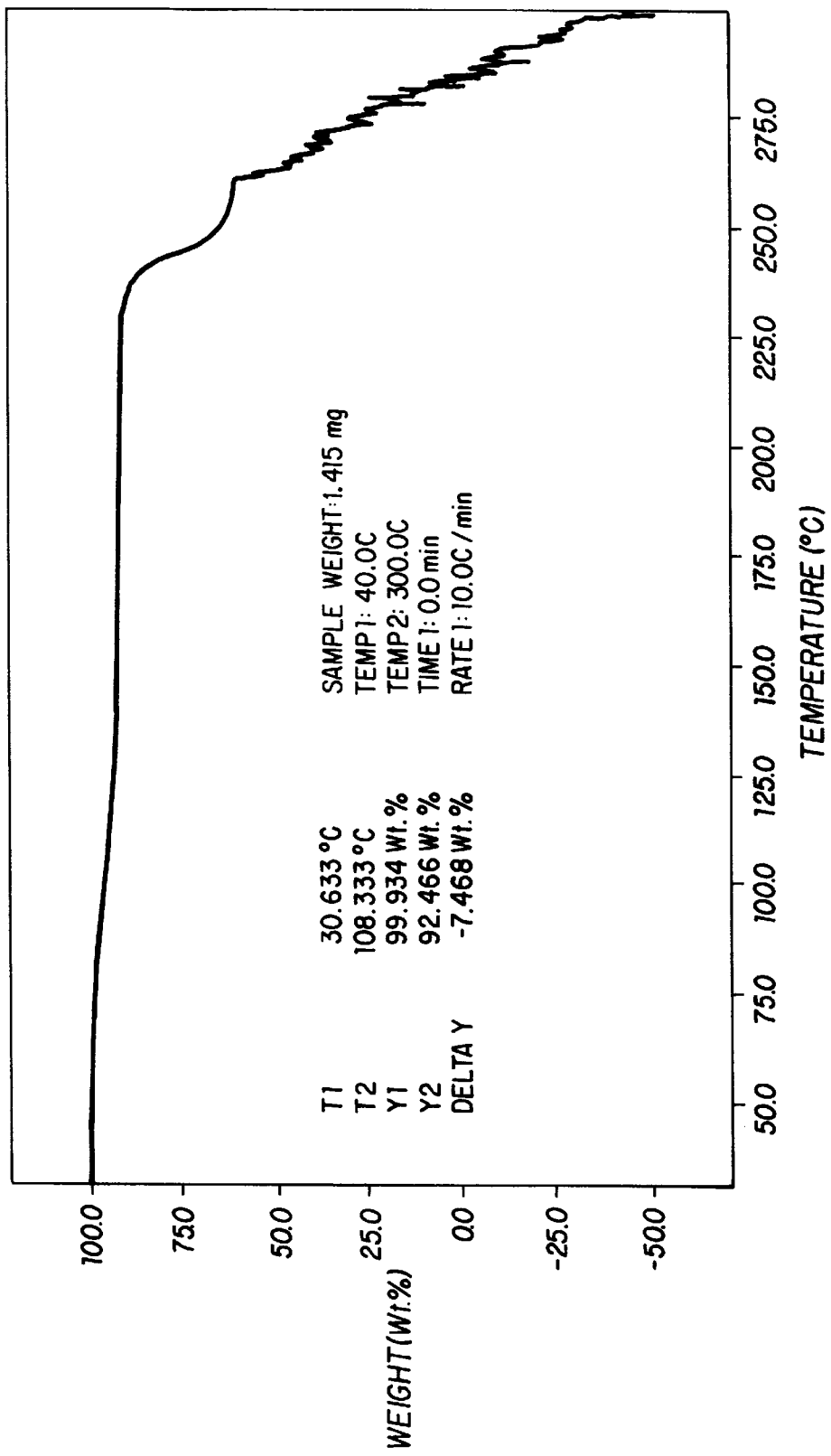
FIG. 6 depicts a TGA for sodium 2',3'-dideoxy-2',3'-didehydrothymidine.
Figure 7:
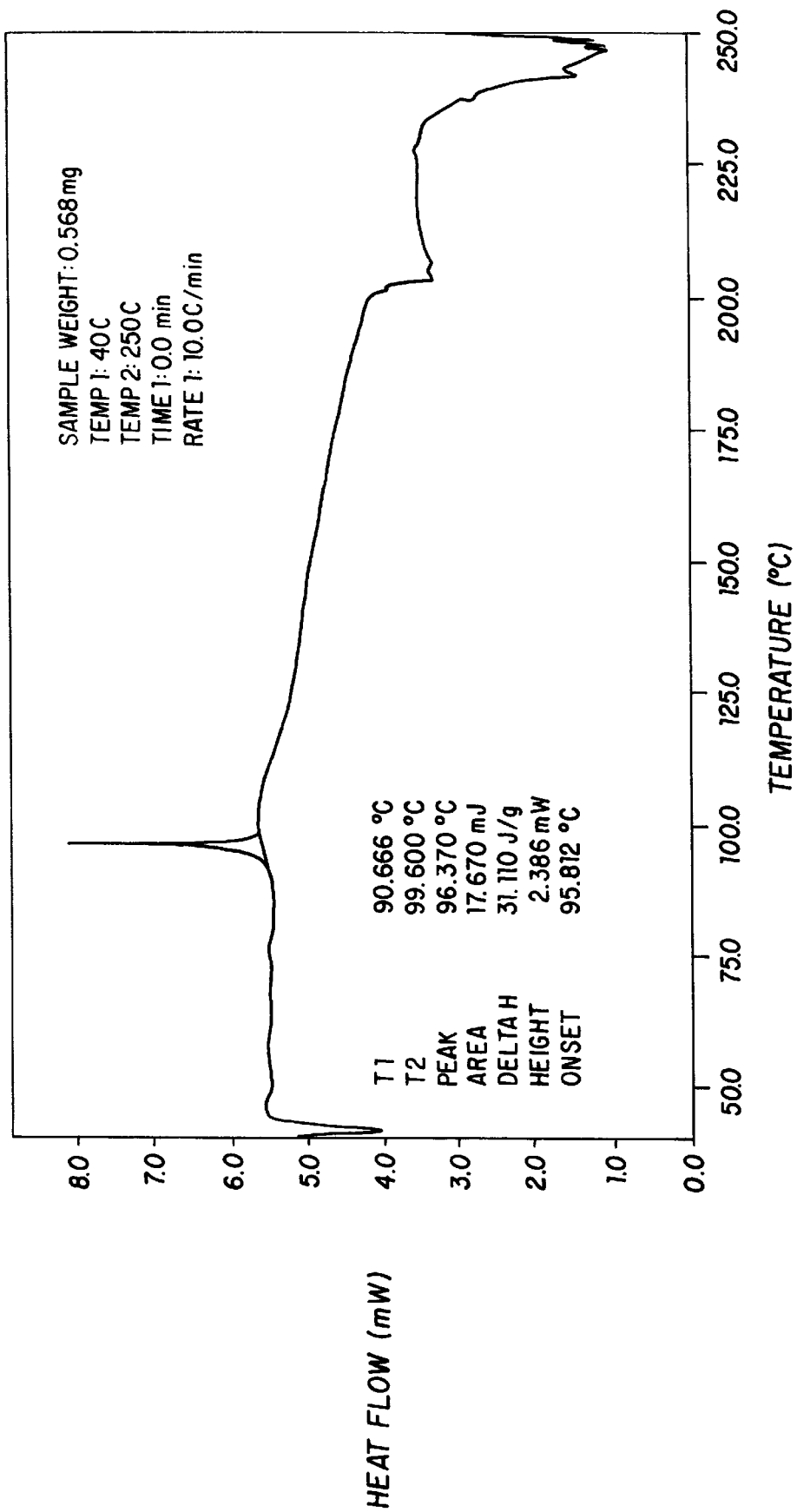
FIG. 7 depicts a DSC for sodium 2',3'-dideoxy-2',3'-didehydrothymidine.

5. IR: See FIG. 1
6. TGA: See FIG. 2
7. DSC: See FIG. 3

8. X-Ray (film):

| X-Ray d-Lines | | | |
|---|---|---|---|
| DDI | | Sodium DDI.H$_2$O | |
| d | I/I$_o$ | d | I/I$_o$ |
| 14.57 | 100 | 8.75 | 60 |
| 8.39 | 80 | 7.82 | 80 |
| 7.46 | 20 | 6.21 | 30 |
| 6.60 | 10 | 5.81 | 20 |
| 6.00 | 20 | 5.28 | 10 |
| 5.50 | 20 | 5.00 | 10 |
| 5.14 | 20 | 4.65 | 40 |
| 4.79 | 30 | 4.22 | 50 |
| 4.46 | 30 | 3.89 | 100 |
| 3.54 | 90 | 3.49 | 20 |
| 3.21 | 40 | 3.25 | 20 |
| 3.04 | 30 | 3.09 | 10 |
| | | 2.92 | 50 |
| | | 2.77 | 10 |
| | | 2.61 | 20 |

Figure 4:
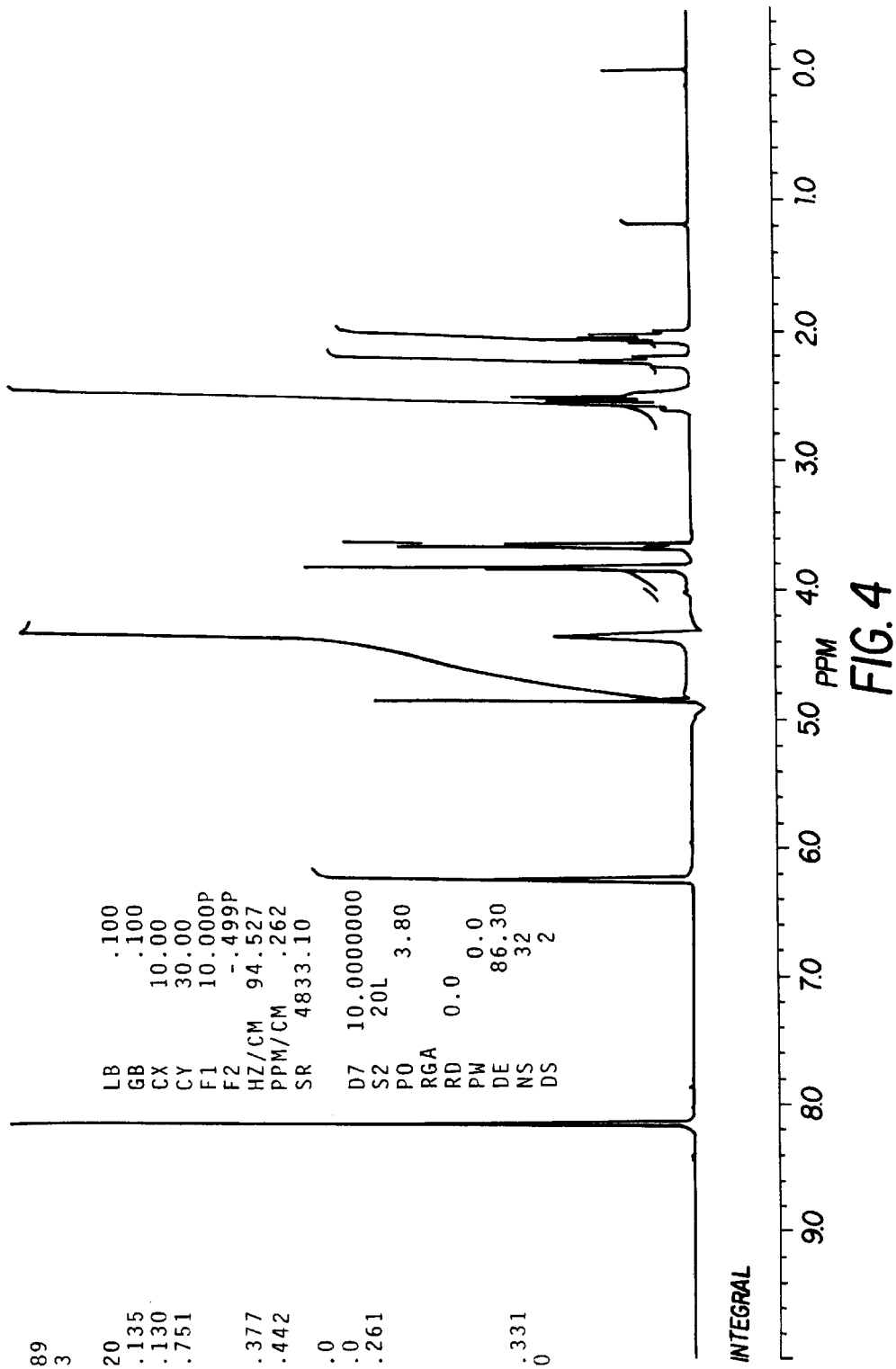
FIG. 4 depicts an NMR for sodium 2',3'-dideoxyinosine.

9. NMR: See FIG. 4 (no solvents present)

TABLE I

| HPLC Assay Method | |
|---|---|
| Column: | IBM Phenyl, 5 micron, 4.5 × 150 nm |
| Mobile Phase: | 98% 0.015M NH$_4$H$_2$PO$_4$ in Milli-Q Water, pH 7.1 with concentrated NH$_4$OH/2% acetonitrile |
| Flow Rate: | 1.0 ml/min in water |
| Approximate Retention Times: | ddI: 10 minutes |
| | Hypoxanthine: 3 minutes |

EXAMPLE 2

Preparation of Sodium d4T Monohydrate

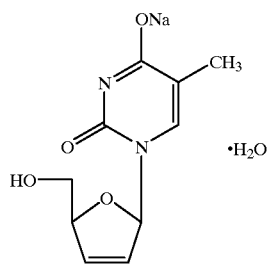

MW: d4T=224.2
MW: NaOH=40

$$\frac{1 \text{ g d4T}}{224.21} = \frac{X}{40} = \frac{178.4 \text{ mg NaOH}}{40} = 4.46 \text{ ml of 1 N NaOH is equivalent to 1 g of d4T for a 1:1 molar ratio.}$$

1. Add with moderate stirring at 15–25° C. over a five minute interval 1 g of d4T to 4.7 ml of aqueous 1 N NaOH (1.05 molar equivalents). A solution (pH 9.5–11) or near solution is obtained.
2. Repeat and follow Steps 2–7 as described in Example 1 for the preparation of sodium DDI-H$_2$O.
3. Expected yield of d4T-H$_2$O=1–1.1 g.

Chemical and Physical Parameters Obtained for Sodium d4T.H$_2$O

1. Water Solubility: >300 mg/ml (pH 9.5–11)
2. Aqueous Solution Stability: 1 week at 50° C.-20% remaining
3. Solid State Stability: No loss for 1 week at 70° C.
4. Elemental Analysis: C$_{10}$H$_{11}$N$_2$O$_4$Na.H$_2$O (C$_{10}$H$_{13}$N$_2$O$_5$Na) MW: 264.22

| | Theory | Found |
|---|---|---|
| % C | 45.5 | 45.05 |
| % H | 5.0 | 4.89 |
| % N | 10.6 | 10.37 |
| % Na | 8.7 | 8.43 |
| % H$_2$O KF | 6.8 (for monohydrate) | 6.9 |

Figure 5:
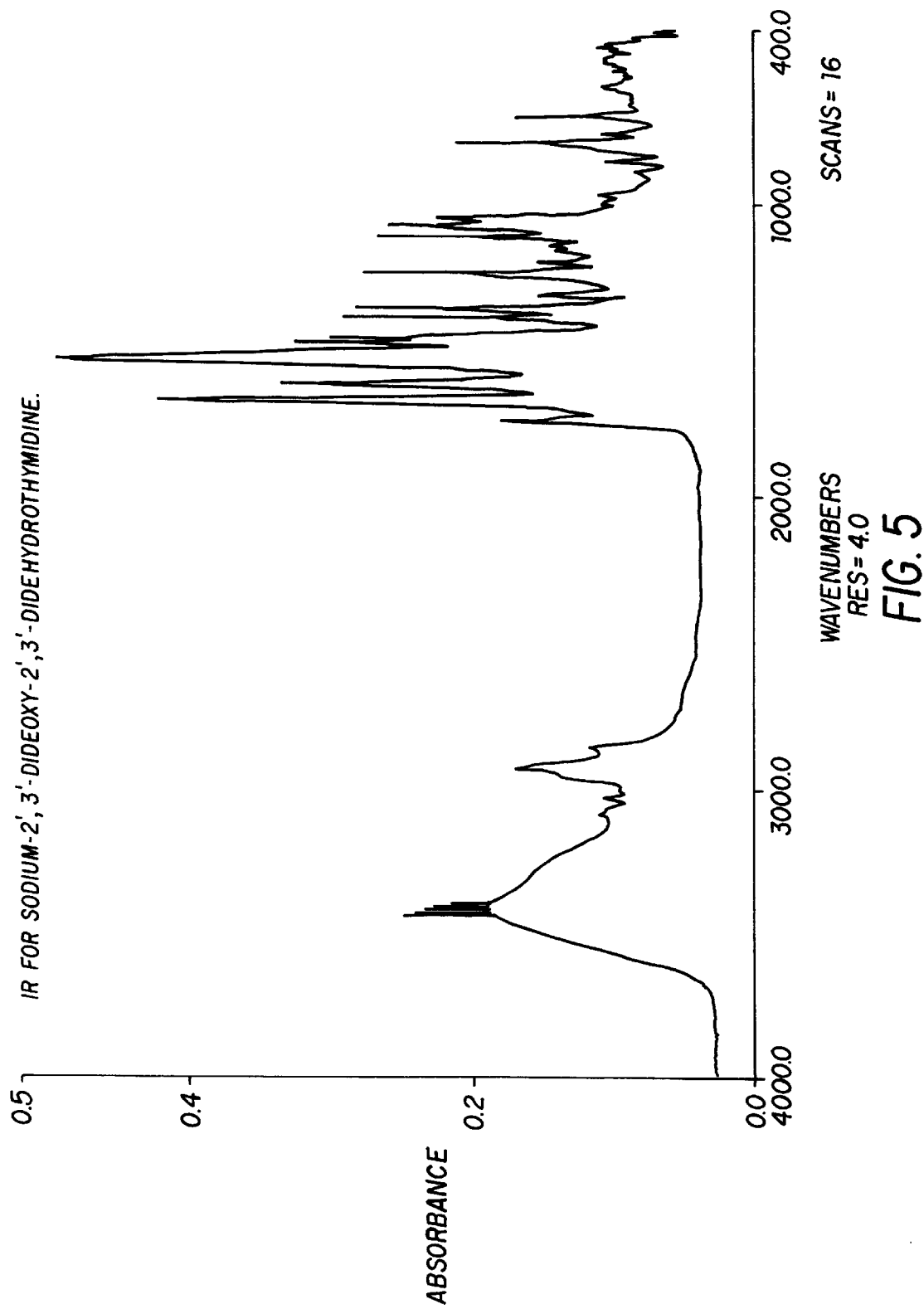
FIG. 5 depicts an IR for sodium 2',3'-dideoxy-2',3'-didehydrothymidine.
Figure 8:
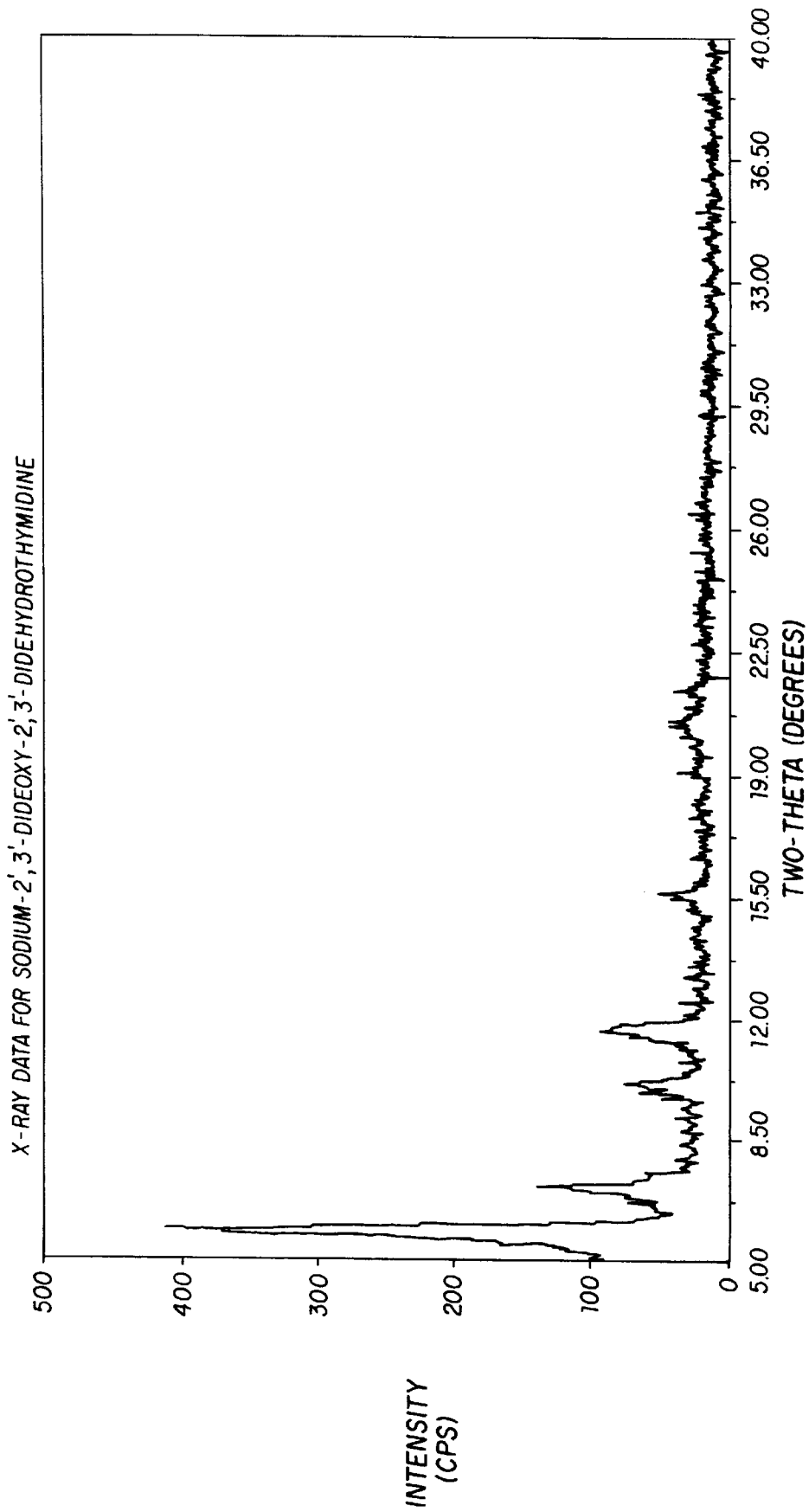
FIG. 8 depicts X-ray data for sodium 2',3'-dideoxy-2',3'-didehydrothymidine.
Figure 9:
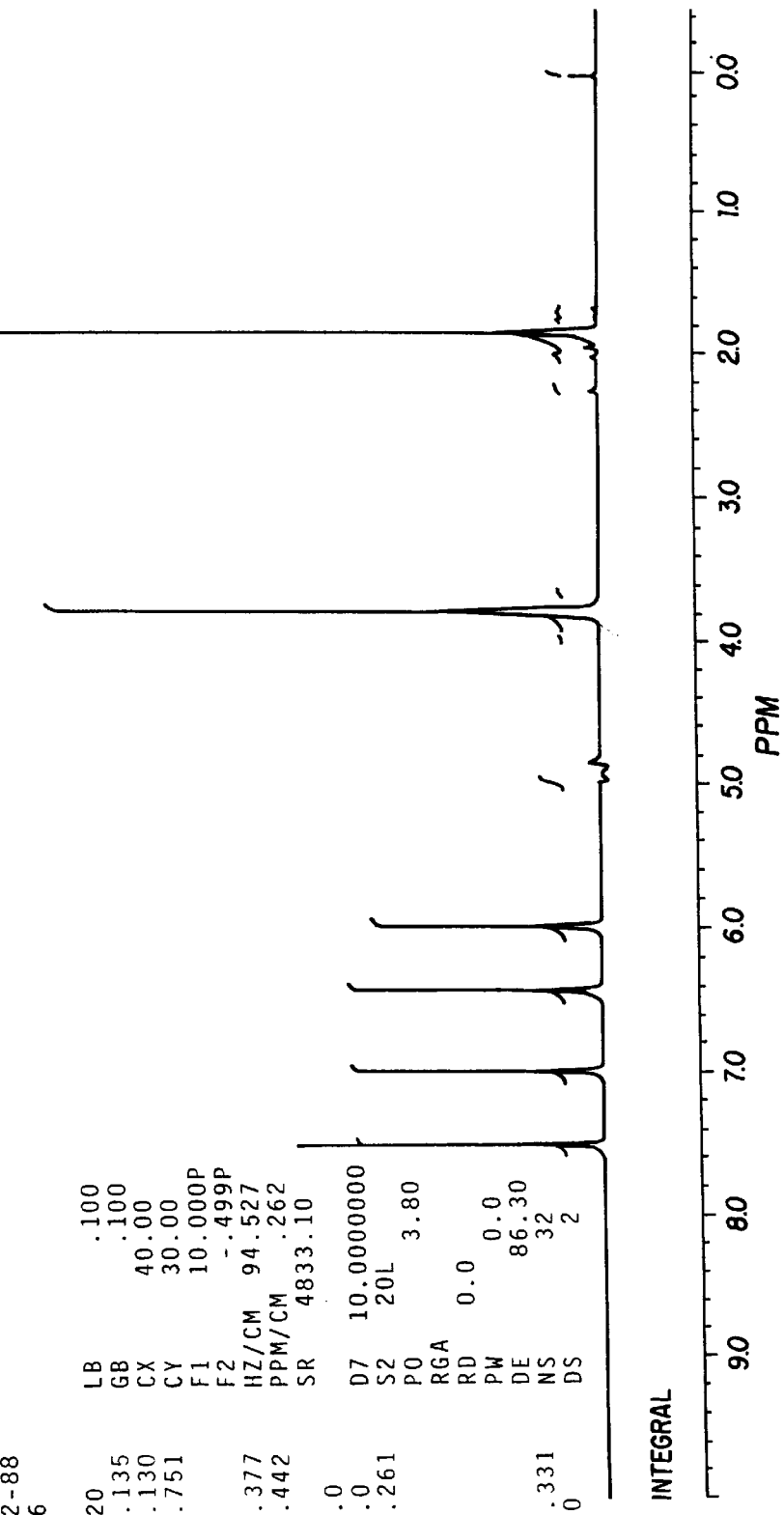
FIG. 9 depicts an NMR for sodium 2',3'-dideoxy-2',3'-didehydrothymidine.

5. IR: See FIG. 5
6. TGA: See FIG. 6
7. DSC: See FIG. 7
8. X-Ray: See FIG. 8

| HPLC Assay Method | |
|---|---|
| Column: | IBM Phenyl, 5 micron, 4.5 × 150 nm |
| Mobile Phase: | 98% 0.015M NH$_4$H$_2$PO$_4$ in Milli-Q Water, pH 7.1 with concentrated NH$_4$OH/2% acetonitrile |
| Flow Rate: | 1.0 ml/minute |
| Injection Volume: | 25 microliter |
| Run Time: | 20 minutes |
| Wavelength: | 254 nm |
| Temperature: | ambient, 20–30° C. |
| Sample Conc.: | approximately 0.1 mg/ml in water |
| Approximate Retention Times: | d4T: 8 minutes |
| | Thymine: 3 minutes |

EXAMPLE 3

Preparation of Sodium F-ddI Hemihydrate

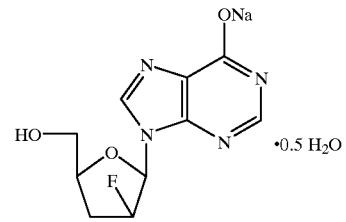

MW: F-ddI=254.24
MW: NaOH=40

$$\frac{436 \text{ mg F-ddI}}{254.24} = \frac{x}{40} = \frac{68.6 \text{ mg NaOH}}{40} = 1.72 \text{ ml of 1 N NaOH is equivalent to 436 mg of FDDI for a 1:1 molar ratio}$$

1. F-ddI (436 mg) was slurried in 1.8 ml of 1 N NaOH (256 mg/ml Na F-ddI). A pH 9.9 solution was obtained in 2 minutes.
2. Two ml of isopropanol was added. The solution remained clear.
3. Isopropanol was added slowly with slurrying. Heavy needle-like crystallization started when 15 ml of isopropanol was added. The mixture was slurried for 10 minutes.

4. Fifteen ml of acetone was added and the mixture was slurried an additional 15 minutes.

5. The crystals were removed by vacuum filtration, washed with 15 ml of acetone and 20 ml of ether, and vacuum-dried ($P_2O_5$ at 50° C. for 2 hours and then at 24° C. for 24 hours). Yield: 430 mg.

A 21 mg sample readily dissolved in 0.05 ml of water (~400 mg/ml; pH 10.0).

Elemental Analysis: $C_{10}H_{10}N_4FO_3Na \cdot \frac{1}{2}H_2O$

|  | Theory | Found |
|---|---|---|
| % C | 42.0 | 41.19 |
| % H | 3.9 | 3.73 |
| % N | 19.6 | 18.8 |
| % F | 6.6 | 6.13 |
| % Na | 8.0 | 8.11 |
| % $H_2O$ KF | 3.23 (hemihydrate) | 3.21 |

X-Ray (film):

| X-Ray d-Lines | |
|---|---|
| d | $I/I_o$ |
| 16.20 | 50 |
| 9.40 | 50 |
| 6.91 | 50 |
| 5.81 | 50 |
| 5.40 | 100 |

Figure 11:
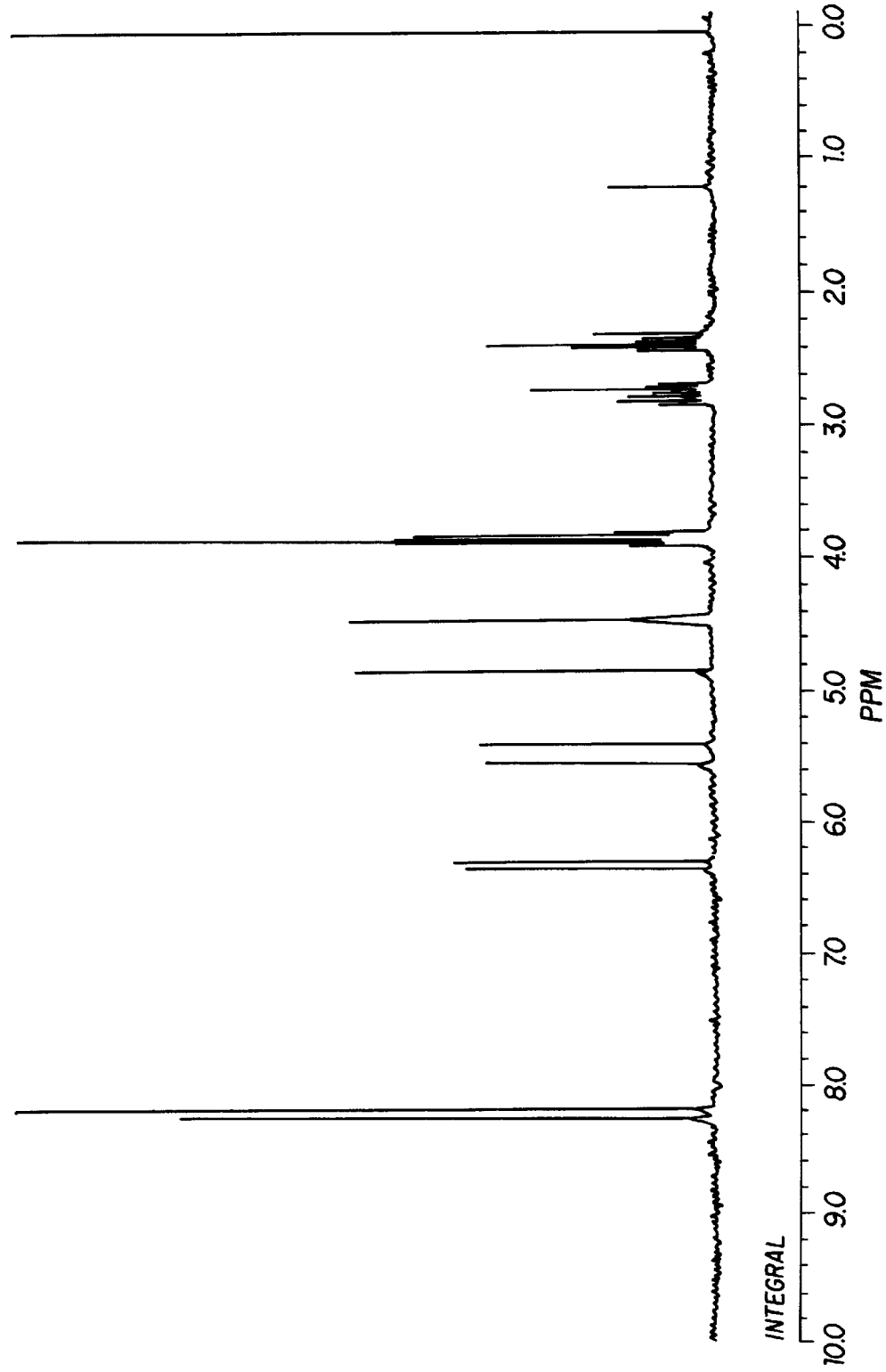
FIG. 11 depicts an NMR for sodium 2',3'-dideoxy-2'-fluoroinosine.

NMR: See FIG. 11. Data consistent with proposed structure.

No acetone or ether present. No α-isomer present.

Figure 10:
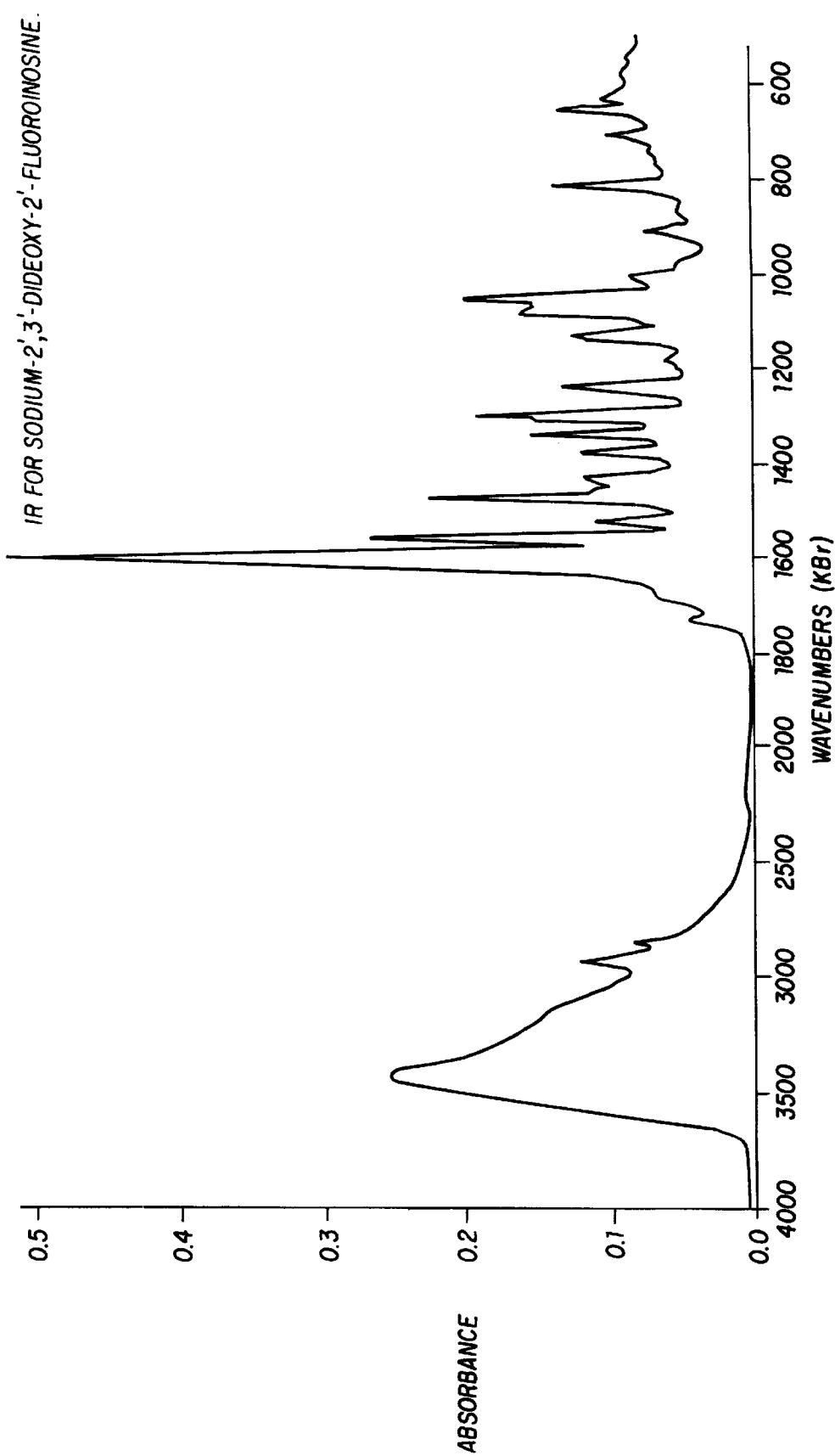
FIG. 10 depicts an IR for sodium 2',3'-dideoxy-2'-fluoroinosine.

IR: See FIG. 10.

Figure 13:
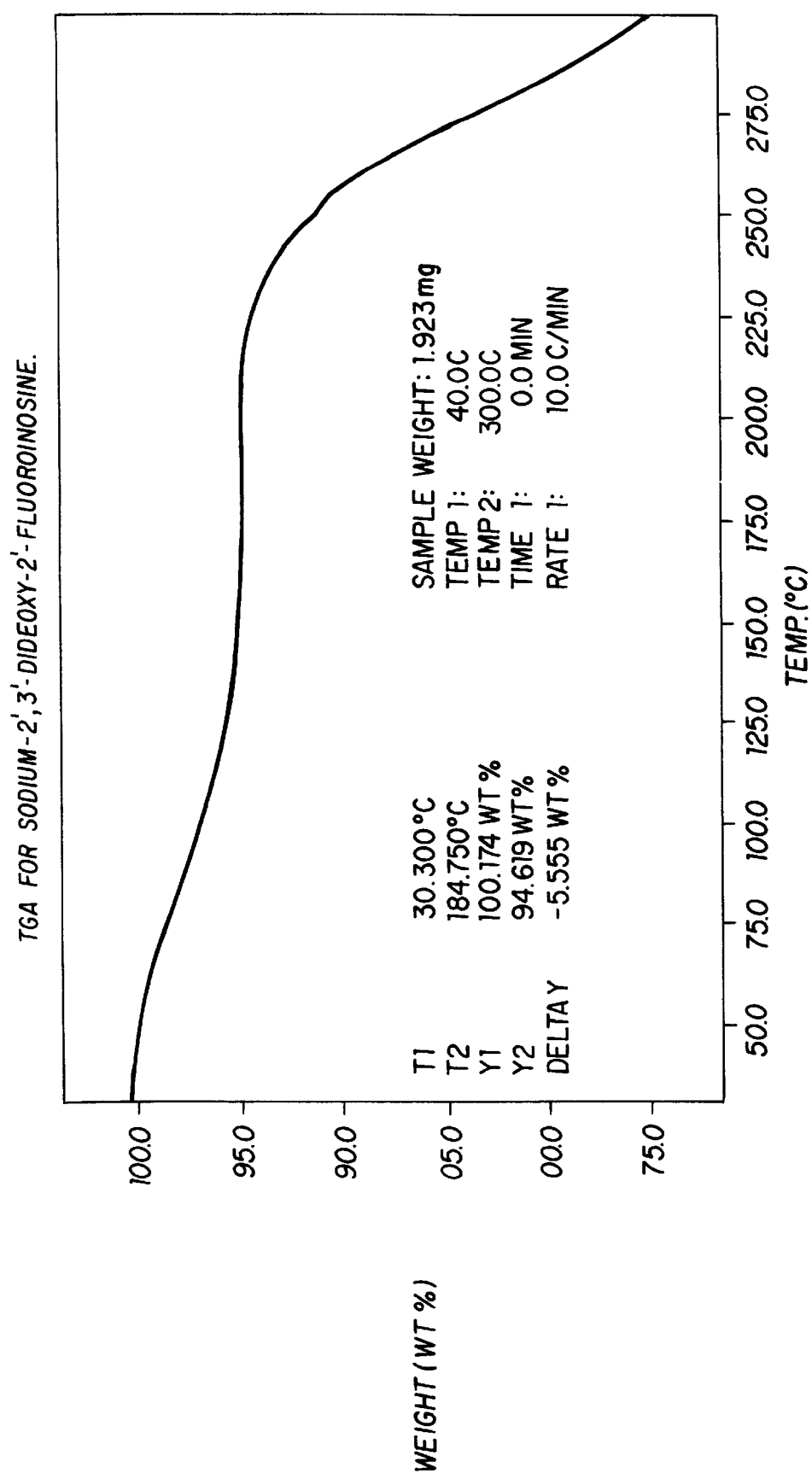
FIG. 13 depicts a TGA for sodium 2',3'-dideoxy-2'-fluoroinosine.

TGA: See FIG. 13.

Figure 12:
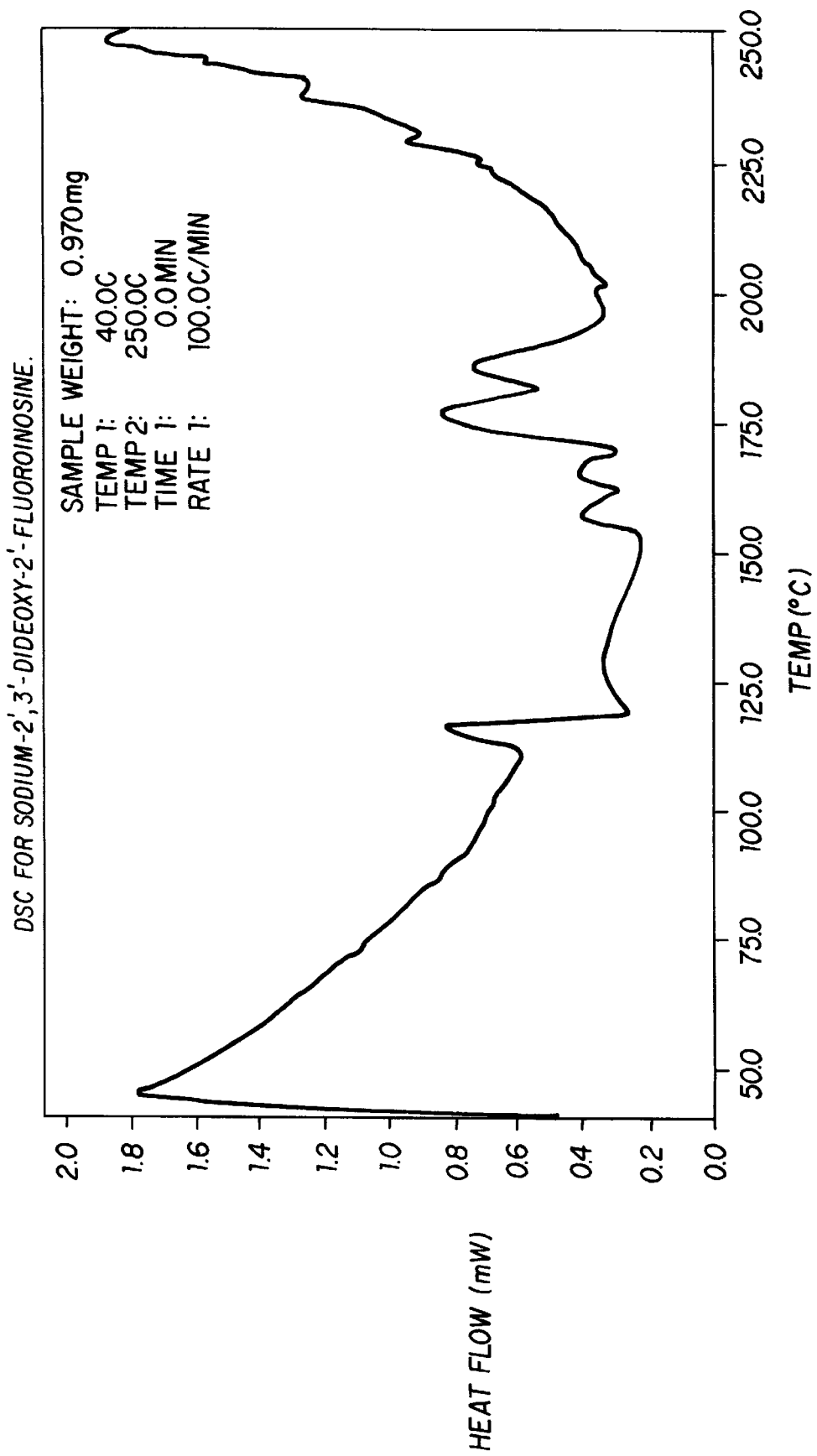
FIG. 12 depicts a DSC for sodium 2',3'-dideoxy-2'-fluoroinosine.

DSC: See FIG. 12.

| HPLC Assay Method | |
|---|---|
| Column: | Supelco #5-8355, 5 micron, 4.6 × 250 mm, LC-18-DB, C18 |
| Mobile Phase: | 95% 0.01M ammonium acetate in Milli-Q water/5% acetonitrile |
| Flow Rate: | 1.0 ml/min |
| Injection Volume: | 20 microliter |
| Run Time: | 25 minutes |
| Wavelength: | 254 nm |
| Temperature: | ambient, 20–30° C. |
| Sample conc.: | ~0.1 mg/ml in $H_2O$ |
| Approximate Retention Times: | F-ddI 7 minutes Hypoxanthine 2 minutes |

Solid State Stability: No loss for 2 weeks at 100° C.

Aqueous Solution Stability: 3% loss for 1 week at 70° C.

EXAMPLE 4

Preparation of Potassium D4T Monohydrate

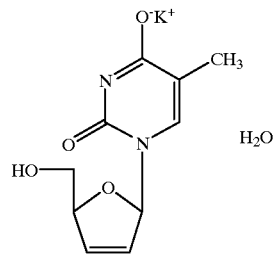

D4T (4.6 g, 0.025 moles) was slurried in 5 ml of Milli-Q water. To the slurry was added with stirring over a four min period 20.5 ml of 1 N KOH to produce a light yellow solution, pH 10.0.

The solution then was added over a 10 min interval to 500 ml of rapidly stirring acetone. A crystalline precipitate is formed and the mixture was allowed to stir for an additional 0.5 hr at 24° C.

The crystals were then isolated on a glass filter by vacuum filtration. The resulting product was washed twice with 75 ml of acetone and dried under high vacuum at 40° C. for three days. The observed yield was 4.2 g. Alternatively, the product may be crystallized from a water/acetone mixture.

Analysis for K: Theory: 14.85%; Found: 15.2%

IR (KBr, cm$^{-1}$): 3396, 2921, 1661, 1609, 1513, 1466, 1444, 1382, 1349, 1301, 1229, 1191, 1107, 1070, 1047, 788.

| X-Ray (Powder diffraction) d-lines: | |
|---|---|
| d | $I/I_o$ |
| 16.7 | 100 |
| 12.4 | 27 |
| 9.86 | 31 |
| 4.55 | 6 |

$H_2O$ content (monohydrate): Theory: 6.4%; Found: 4.8%

Stability: The product remained stable for at least 56 days at 50° C.

Solubility: >200 mg/ml

EXAMPLE 5

Preparation of Potassium ddI ddI (4.36 g, .0196 moles) were suspended in 30 ml of Milli-Q water. To the suspension were added with moderate stirring at 24° C. over a five min interval 1 N KOH (19.6 ml) to obtain a pH 10.0 solution.

The solution was added, over 5 minutes, to rapidly stirring acetone (1 L) to produce a viscous glue-like precipitate. The supernatant was decanted and replaced with fresh acetone (500 ml).

The mixture was stirred vigorously for 24 hrs at 24° C. after which the precipitate converted to gel-like crystals. The crystals were removed by vacuum filtration, washed with acetone (100 ml) and vacuum dried over $P_2O_5$ at 50° C. for 24 hours. Yield: 3 g.

IR (KBr, cm$^{-1}$): 1596, 1557, 1519, 1470, 1331, 1295, 1228, 1123, 1062, 809

X-ray (Powder diffraction) d lines:

| d | I/I$_o$ |
|---|---|
| 13.16 | 85 |
| 8.89 | 65 |
| 5.43 | 59 |
| 3.51 | 100 |
| 3.29 | 86 |
| 2.84 | 50 |

EXAMPLE 6

Preparation of Potassium ddI Hemihydrate

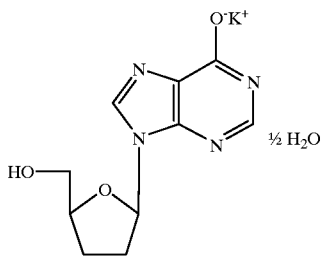

To 20 ml of Milli-Q water at 24° C. was added ddI (4.8 g, 0.0177 moles). To the resulting slurry was added, over a 3 min interval, 1 N KOH (17.7 ml) to produce a pH 10.1 solution.

The solution was cooled to −40° F. in a type I flint glass vial and the product was lyophilized at a temperature of −10° F. for 24 hrs, and then at 75° F. for 24 hrs.

The resulting lyophile was slurried with acetone (125 ml) for 1 hr at 24° C. and the gelled crystals were removed by vacuum filtration, washed with acetone (50 ml) and dried in vacuo at 50° C. over P$_2$O$_5$ for 4 hrs. Yield: 3.9 g.

Analysis for K: Theory, 14.2%; Found: 14.2%

Water content (hemi-hydrate): Theory, 3.1%; Found, 2.93%

IR (KBr, cm$^{-1}$): 1598, 1557, 1519, 1471, 1331, 1294, 1229, 1123, 1061, 809

It will be appreciated that the instant specification and claims are set forth by way of illustration and not limitation, and that various modifications and changes may be made without departing from the spirit and scope of the present invention.

We claim:

1. A highly water soluble, stable, crystalline salt of 2',3'-dideoxy-2',3'-didehydrothymidine of Formula (I):

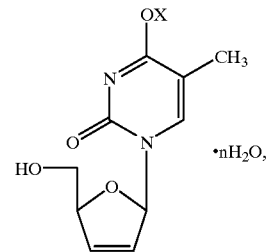

wherein X is an alkali or alkaline earth metal ion, an ammonium ion or a quaternary amino ion and n is 0.5 to 2.0.

2. A salt according to claim 1, wherein X is Na$^+$ or K$^+$.

3. Sodium 2',3'-dideoxy-2',3'didehydrothymidine monohydrate.

4. Potassium 2',3'-dideoxy-2',3'-didehydrothymidine monohydrate.

5. A pharmaceutical composition comprising an antiviral effective amount of a salt according to claim 1 and a physiological acceptable solid or liquid diluent.

6. A method of treating a mammal infected with a virus comprising administering to said warm blooded animal an antiviral effective amount of a salt according to claim 1, either alone or in admixture with a diluent or in the form of a medicament.

7. A method according to claim 6 wherein the salt is a medicament in the form of a tablet, capsule or powder for oral administration and is enteric coated or buffered against gastric acid.

8. A highly water soluble, stable, crystalline sodium salt of 2',3'-dideoxyinosine of Formula (II):

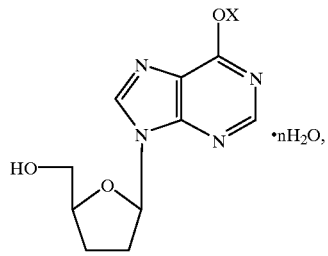

wherein X is an alkali or alkaline earth metal ion, an ammonium ion or a quaternary amino ion and n is 0.5 to 2.0.

9. A salt according to claim 8, wherein X is Na$^+$ or K$^+$.

10. Sodium 2',3'-dideoxyinosine monohydrate.

11. Potassium 2,3'-dideoxyinosine hemihydrate.

12. A soluble, self-buffering pharmaceutical composition comprising an antiviral effective amount of a salt according to claim 8 and a physiologically acceptable solid or liquid diluent.

13. A method of treating a mammal infected with a virus comprising administering to said warm blooded animal an antiviral effective amount of a salt according to claim 8, either alone or in admixture with a diluent or in the form of a medicament.

14. A method according to claim 13, wherein the salt is a medicament in the form of a tablet, capsule for powder for oral administration and is enteric coated or buffered against gastric acid.

15. A highly water-soluble, stable, crystalline salt of 2',3'-dideoxy-2'-fluoroinosine of Formula (III):

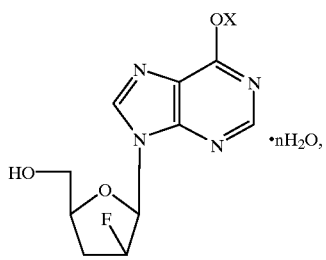

(III)

wherein X is an alkali or alkaline earth metal ion, an ammonium ion or a quaternary amino ion and n is 0.5 to 2.0.

16. A salt according to claim 15, wherein X is Na$^+$.

17. A salt according to claim 16 wherein n is 0.5.

18. Sodium 2',3'-dideoxy-2'-fluoroinosine hemihydrate.

19. A soluble, self-buffering pharmaceutical composition containing an antiviral effective amount of a salt according to claim 15 and a pharmaceutically acceptable carrier.

20. A method of treating a mammal infected with a virus comprising administering to said warm-blooded animal an antiviral effective amount of a salt according to claim 15, either alone or in admixture with a pharmaceutically acceptable carrier.

21. A method according to claim 20 wherein the salt is a medicament in the form of a tablet, capsule or powder for oral administration and is enteric coated or buffered against gastric acid.

22. A method of treating a viral infection comprising contacting the virus with an antiviral amount of the compound of claim 1.

23. A method of treating a viral infection comprising contacting the virus with an antiviral amount of the compound of claim 8.

24. A method of treating a viral infection comprising contacting the virus with an antiviral amount of the compound of claim 15.

* * * * *